United States Patent [19]

Meyers et al.

[11] Patent Number: 4,910,152

[45] Date of Patent: Mar. 20, 1990

[54] METHOD FOR BINDING OPIOID RECEPTORS

[76] Inventors: Vera K. Meyers, University of Wisconsin-Parkside, Greenquent Hall, Box No. 2000, Kenosha, Wis. 53141; Ahmet Koman, Väktarg 4C, 75422 Uppsala, Sweden

[21] Appl. No.: 869,737

[22] Filed: Jun. 2, 1986

Related U.S. Application Data

[63] Continuation-in-part of Ser. No. 697,212, Jan. 31, 1985, Pat. No. 4,678,779.

[51] Int. Cl.$^4$ ............... G01N 33/566; G01N 33/534; A61K 43/00; C12Q 1/04
[52] U.S. Cl. ..................... 436/501; 436/504; 436/545; 436/546; 436/800; 436/804; 436/805; 436/816; 424/1.1; 435/34; 435/35; 514/282

[58] Field of Search ............... 424/1.1; 435/34, 35; 436/501, 504, 545, 546, 800, 804, 805, 816; 514/282

[56] References Cited

U.S. PATENT DOCUMENTS 4,767,718 8/1988 Meyers ..................... 436/501

Primary Examiner—Robert J. Warden
Assistant Examiner—Jack Spiegel
Attorney, Agent, or Firm—Senniger, Powers, Leavitt and Roedel

[57] ABSTRACT

A method of controlling weight in a mammal and diagnosing, treating, and preventing disorders associated with delta-type opioid receptors comprising administering to the mammal a receptor probe or a weight control agent for inhibiting weight gain. The receptor probe or weight control agent may comprise certain azine, thiosemicarbazone, or N,N'-disubstituted thiourea derivatives of nonpeptide opioid antagonists.

1 Claim, 2 Drawing Sheets

METHOD FOR BINDING OPIOID RECEPTORS

CROSS-REFERENCE TO RELATED APPLICATION

This application is a continuation-in-part of copending application Ser. No. 697,212, filed Jan. 31, 1985.

BACKGROUND OF THE INVENTION

This invention relates to the field of opioid receptor probes, and more particularly to a novel method for binding opioid receptors by administration to mammals of a long lasting opioid receptor probe comprising a non-peptide opioid antagonist and another moiety.

While opiates are important in pain perception and induce various behavioral and regulatory effects, the term opioid is used in a broader sense to denote all compounds, including endogenous peptides, that act directly on opioid receptors. Opioid receptors, which are found in both the central nervous system and the peripheral nervous system, were first postulated by Beckett and Casey in 1953, and their existence confirmed in 1973, as described by Terenius, L., in "Stereospecific interaction between narcotic analgesics and a synaptic plasma membrane fraction of rat cerebral cortex," Acta Pharmac. Toxic. 32: 317-320 (1973), Simon, E. J., et al., in "Stereospecific binding of the potent narcotic analgesic ($^3$H)Etorphine to rat-brain homogenate," Proc. Natl. Acad. Sci. USA 70: 1947-1949 (1973), and Pert, C. B. and Snyder, S. H., in "Opiate receptor: Demonstration in nervous tissue," Science 179: 1011-1014 (1973).

Previous studies have suggested that endogenous opioids may be involved in the control of feeding and appetite. See, for example, H. N. Bhargava, "Opiate Agonists and Antagonists: Pharmacological, Behavioral, and Neurochemical Effects of Stereoisomers," in "CRC Handbook of Stereoisomers: Drugs in Psychopharmacology", D. F. Smith, Ed., CRC Press, Boca Raton, Fla., 1984, pp. 401-439, and the references cited therein. In particular, it has been demonstrated that the administration of naloxone reduces food intake in animals (for example, mice, rats, guinea pigs, squirrel monkeys) and humans by blockage of opiate receptors, Bhargava, supra; Herman and Holtzman, Life Sci., 34, 1-12 (1984). Yim and Lowy, "Opioids, Feeding, and Anorexias", Federation Proceedings Vol. 43, 14, pp. 2893-2897 (November 1984), reported that administration of the opioid antagonists naloxone and naltrexone were effective in suppressing feeding that had been induced by administration of 2-deoxy-D-glucose.

Hahn, Pasternak et al., J. Neuroscience, 2, 572-576 (1982), discovered that the opiate antagonist naloxone azine has a long lasting effect, i.e., that it is removed only very slowly after having been bound to the sites of opioid receptors. However, Hahn et al. did not disclose any possible use of naloxone azine as a weight control agent.

Other studies of opioid receptor properties have identified several types of receptors, including mu-receptors, kappa-receptors and delta-receptors. Mu-receptors have been associated mainly with sensory systems involving pain, and preferentially bind morphine and most other opiates. Kappa-receptors appear to be involved in analgesia and other central nervous system and peripheral nervous system functions, and bind dynorphins and certain benzomorphans. The classical antagonist naloxone and its congeners are relatively nonselective, but have highest affinities for mu-receptors.

Enkephalins and endorphins are endogenous opioid peptides that are known to interact preferentially with delta-receptors. Delta receptors have been associated with several central nervous system effects, particularly pertaining to the limbic system. It is believed that it is specifically the delta-type opioid receptors that are involved in weight control. Aside from their role in weight regulation, delta-type opioid receptors and endogenous endorphins have been associated with various disorders ranging from epilepsy and schizophrenia to pre-menstrual syndrome. See, for example, Peck, J. Amer. Osteop. Assoc., 82: 192 (1982), and Halbreich and Endicott, Medical Hypotheses, 7: 1045 (1981) with respect to pre-menstrual syndrome. Although certain enkephalin derivatives have been used as delta-selective opioid antagonists, they have several drawbacks as in vivo probes. For example, since enkephalins are peptides, they are metabolically unstable and do not easily cross the blood/brain barrier.

Naloxone has been used to treat pre-menstrual syndrome (see Peck, supra), but has precipitated opioid withdrawal symptoms. It is believed that the withdrawal symptoms result from the relatively large and abrupt dose of naloxone employed for such purposes. Such large concentrated doses are believed necessary for treatment of pre-menstrual syndrome because naloxone is neither delta-selective nor long lasting.

In the development of compositions and methods for weight control and for treatment or prevention of disorders associated with delta-type opioid receptors, there is a need for anorexic or other weight control agents or other opioid receptor probes which are long lasting, generally non-toxic, and substantially free of any other adverse side effects. There is a particular need for compositions which may be administered orally to provide persistent control of weight or treatment or prevention of disorders associated with delta-type opioid receptors, without toxic effects on the recipient.

To locate, identify and determine the concentration of the delta-type of receptors, and to diagnose disorders associated with delta-type opioid receptors, a need exists for improved receptor probes that are long lasting, generally non-toxic, and substantially free of adverse side effects. There is a particular need for compositions which may be administered in vivo to produce persistent and selective blocking of delta-receptors without toxic effects on the recipient.

SUMMARY OF THE INVENTION

Among the several objects of the present invention, therefore, may be noted the provision of an improved method for inhibition of weight gain in mammals; the provision of such a method which provides a persistent and even effect on food intake and utilization; the provision of such a method which produces no significant toxic or other unfavorable side effects on the recipient; the provision of such a method in which a weight control agent is administered orally to the recipient; and the provision of novel compositions useful in such method of inhibition of weight gain.

Additional objects of the invention include the provision of an improved method for identifying, locating and determining the concentration of delta-type opioid receptors; the provision of such a method which produces no significant toxic or other unfavorable side effects on the recipient; the provision of such a method wherein the effect is long lasting; and the provision of a method for diagnosing disorders associated with delta-type opioid receptors.

Further objects of the invention include the provision of a method for treating disorders associated with delta-type opioid receptors; the provision of such a method which produces no significant toxic or other unfavorable side effects on the recipient; and the provision of such a method wherein the therapeutic or prophylactic effect is long lasting.

Briefly, therefore, the present invention is directed to a novel method for controlling weight in a mammal. In this method, a weight control agent for inhibiting weight gain is administered to the mammal, the agent being selected from among:

$$A{=}N{-}N{=}R^1 \qquad \text{(Formula I)}$$

$$X{=}N{-}N{=}Y{=}N{-}N{=}R^1 \qquad \text{(Formula II)}$$

$$\text{Fl}{-}\text{NH}{-}\overset{\overset{\displaystyle S}{\|}}{C}{-}\overset{\overset{\displaystyle H}{|}}{N}{-}N{=}R^1, \text{ and} \qquad \text{(Formula III)}$$

$$\text{Fl}{-}\text{NH}{-}\overset{\overset{\displaystyle S}{\|}}{C}{-}\text{NH}{-}R^2 \qquad \text{(Formula IV)}$$

where $R^1$ comprises a divalent nonpeptide opioid antagonist, $R^2$ comprises a monovalent nonpeptide opioid antagonist, A is selected from among steroid moieties and fluorescent moieties, X is selected from among nonpeptide opioid antagonists and fluorescent moieties, Y comprises a steroid moiety, and Fl comprises a fluorescent moiety.

The invention is further directed to a weight control preparation adapted for administration to a mammal for inhibition of weight gain. The preparation comprises a weight control agent selected from among Formulae I to IV, above, and a pharmaceutically acceptable carrier, excipient or adjuvant.

The invention is also directed to compounds corresponding to Formulae II and IV; and further to compounds corresponding to the formula $$A^1{=}N{-}N{=}R^1 \qquad \text{(Formula VII)}$$

where $A^1$ comprises a steroid moiety.

The invention is further directed to a novel method for locating, identifying or determining the concentration of delta-type opioid receptors in a mammal. In the method, a radio-labeled, long lasting, non-peptide receptor probe comprising a compound corresponding to the formula:

$$A{=}N{-}N{=}R^1 \qquad \text{(Formula I)},$$

where A is selected from among steroid moieties and fluorescent moieties, and $R^1$ comprises a divalent nonpeptide opioid antagonist is administered to a mammal. Then, the radiation pattern exhibited by said mammal, which provides an indication of the location, identity or concentration of delta-type opioid receptors in the mammal, is observed.

The invention is further directed to a novel method for diagnosing disorders associated with delta-type opioid receptors. In the method, delta-type opioid receptors are selectively and preferentially blocked by administering to a mammal a radio-labeled, long lasting, nonpeptide receptor probe, said probe comprising a compound corresponding to the formula:

$$A{=}N{-}N{=}R^1 \qquad \text{(Formula I)}$$

where A is selected from among steroid moieties and fluorescent moieties, and $R^1$ comprises a divalent nonpeptide opioid antagonist. Then, the radiation pattern exhibited by said mammal is observed, the indicated location, identity or concentration of delta-type opioid receptors in the mammal providing an indication of the existence and nature of any disorder associated with delta-type opioid receptors that is suffered by the mammal.

The invention is further directed to a novel method for treating or preventing disorders associated with delta-type opioid receptors. In the method, delta-type opioid receptors are selectively and preferentially blocked by administering to a mammal a long lasting, non-peptide receptor probe, said probe being selected from the group consisting of compounds corresponding to the following formulae:

$$A{=}N{-}N{=}R^1 \qquad \text{(Formula I)}$$

$$X{=}N{-}N{=}Y{=}N{-}N{=}R^1 \qquad \text{(Formula II)}$$

$$\text{Fl}{-}\text{NH}{-}\overset{\overset{\displaystyle S}{\|}}{C}{-}\overset{\overset{\displaystyle H}{|}}{N}{-}N{=}R^1, \text{ and} \qquad \text{(Formula III)}$$

$$\text{Fl}{-}\text{NH}{-}\overset{\overset{\displaystyle S}{\|}}{C}{-}\text{NH}{-}R^2 \qquad \text{(Formula IV)}$$

where $R^1$ comprises a divalent nonpeptide opioid antagonist, $R^2$ comprises a monovalent nonpeptide opioid antagonist, A is selected from among steroid moieties and fluorescent moieties, X is selected from among nonpeptide opioid antagonists and fluorescent moieties, Y comprises a steroid moiety, and Fl comprises a fluorescent moiety.

The invention is further directed to a novel in vitro method for locating, identifying or determining the concentration of delta-type opioid receptors in a sample of tissue, cells, or subcellular particles. In the method, the sample is contacted with a labeled, long-lasting, non-peptide receptor probe, said probe comprising a compound corresponding to the formula:

$$A{=}N{-}N{=}R^1 \qquad \text{(Formula I)}$$

where A is selected from among steroid moieties and fluorescent moieties, and $R^1$ comprises a divalent nonpeptide opioid antagonist. Then, the emission pattern exhibited by said mammal, which provides an indication of the location, identity or concentration of delta-type opioid receptors in the sample, is observed.

The invention is further directed to a novel method for treating or preventing disorders associated with excessive binding of endorphins. In the method, delta-type opioid receptors are selectively and preferentially blocked by administering to a mammal having, or having a predisposition to, excessive binding of endorphins or an elevated level of endorphins a long lasting, nonpeptide receptor probe. The probe is selected from the group consisting of compounds corresponding to the formulae:

$$A=N-N=R^1 \quad \text{(Formula I)}$$

$$X=N-N=Y=N-N=R^1 \quad \text{(Formula II)}$$

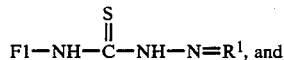
(Formula III)

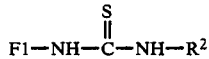
(Formula IV)

where $R^1$ comprises a divalent nonpeptide opioid antagonist, $R^2$ comprises a monovalent nonpeptide opioid antagonist, A is selected from the group consisting of steroid moieties and fluorescent moieties, X is selected from the group consisting of nonpeptide opioid antagonists and fluorescent moieties, Y comprises a steroid moiety, and Fl comprises a fluorescent moiety.

Other objects and features will be in part apparent and in part pointed out hereinafter.

DESCRIPTION OF THE PREFERRED EMBODIMENTS

Figure 1:
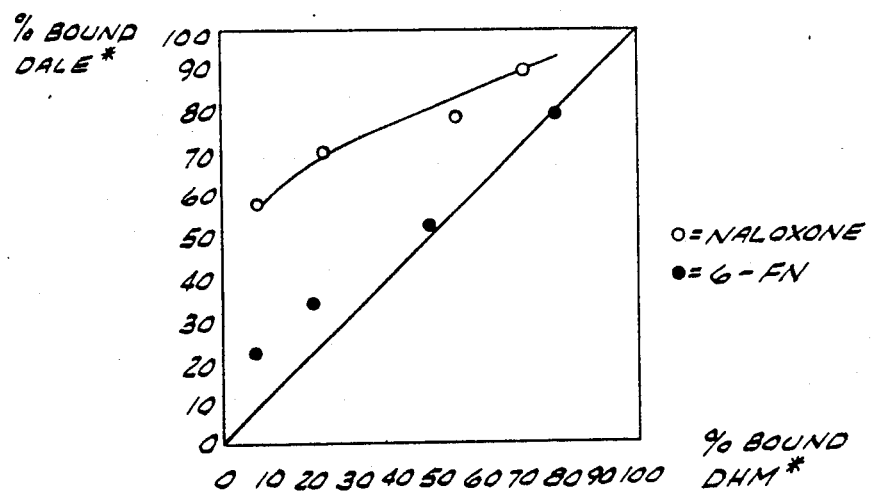
FIG. 1 is a plot comparing the extent of displacement of two different radiolabeled indicator ligands in opioid receptor site selectivity tests conducted on 1-(N)-fluoresceinyl naloxone thiosemicarbazone ("6-FN").

In accordance with present invention it has been discovered that long lasting suppression of weight gain can be achieved by administration to a mammal of a weight control agent comprising certain azine, thiosemicarbazone, or N,N'-disubstituted thiourea derivatives of nonpeptide opioid antagonists. Particular compounds which are effective for this purpose include hybrid (mixed) azines of an opioid antagonist and a steroid:

$$A=N-N=R^1 \quad \text{(Formula I)}$$

where A is selected from among steroid moieties and fluorescent moieties and $R^1$ is a divalent nonpeptide opioid moiety; mixed azines of an opioid antagonist and flourescent moiety:

$$Fl=N-N=R^1 \quad \text{(Formula VIII)}$$

where Fl comprises a fluorescent moiety; steroid bis-(opioid azine)s and other mixed diazines:

$$X=N-N=Y=N-N=R^1 \quad \text{(Formula II)}$$

where Y comprises a steroid moiety and X is either an opioid or fluorescent moiety; thiosemicarbazones of an opioid antagonist and a fluorescent moiety:

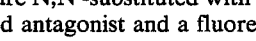
(Formula III)

where Fl comprises a fluorescent moiety, and thioureas that are N,N'-substituted with a monovalent nonpeptide opioid antagonist and a fluorescent moiety:

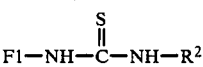
(Formula IV)

where $R^2$ is a monovalent nonpeptide opioid moiety.

It is preferred that the opioid moieties $R^1$ and $R^2$ comprise a normorphinan, normorphine (4,5-epoxymorphinan), or benzonormorphinan structure, most preferably a morphine structure corresponding to the formula

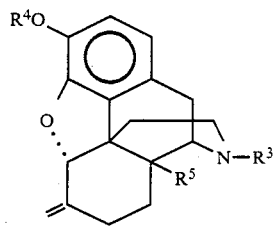
(Formula V)

or

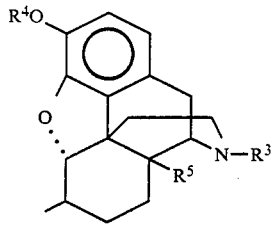
(Formula VI)

where $R^3$ comprises hydrogen, alkyl, alkenyl or an alicyclic substituent, $R^4$ comprises hydrogen, alkyl or acyl, and $R^5$ comprises hydrogen, hydroxyl or acyloxy. Most preferably, $R^4$ comprises either hydrogen or methyl, $R^5$ hydroxyl, and $R^3$ either allyl or cyclopropylmethyl.

It has further been discovered that locating, identifying or determining the concentration of delta-type opioid receptors in a mammal may be accomplished by administering to a mammal a radio-labeled, long lasting, nonpeptide receptor probe and observing the radiation pattern exhibited by said mammal, which pattern provides an indication of the location, identity or concentration of delta-type opioid receptors in the mammal. The receptor probe comprises a compound corresponding to the formula:

$$A=N-N=R^1 \quad \text{(Formula I)}$$

where $A^1$ comprises a steroid moiety and $R^1$ comprises a divalent nonpeptide opioid antagonist, typically in a pharmaceutically acceptable carrier.

It has further been discovered that diagnosing disorders associated with delta-type opioid receptors may be achieved by selectively and preferentially blocking delta-type opioid receptors by administering to a mammal a radio-labeled, long lasting, non-peptide receptor probe, and observing the radiation pattern exhibited by said mammal, which pattern provides an indication of the location, identity or concentration of delta-type opioid receptors in the mammal. In turn, such data on the delta-type opioid receptors in the mammal provides an indication of the existence and nature of any disorder associated with delta-type opioid receptors that may be suffered by the mammal. The probe comprises a compound corresponding to the formula:

$$A=N-N=R^1 \quad \text{(Formula I)}$$

where A is selected from among steroid moieties and fluorescent moieties, and $R^1$ comprises a divalent non-peptide opioid antagonist.

It has also been discovered that treating disorders associated with delta-type opioid receptors may be achieved by selectively and preferentially blocking delta-type opioid receptors by administering to a mammal a long lasting, non-peptide receptor probe. The probe is selected from among the compounds corresponding to any of Formulae I-IV.

It has further been discovered that locating, identifying or determining the concentration of delta-type opioid receptors in a sample of tissue, cells, or subcellular particles, in vitro, may be achieved by contacting the sample with a labeled, long-lasting, non-peptide receptor probe, and observing the emission pattern exhibited by said mammal, which pattern provides an indication of the location, identity or concentration of delta-type opioid receptors in the sample. The probe comprises a compound corresponding to the formula:

$$A=N-N=R^1 \quad \text{(Formula I)}$$

where A is selected from among steroid moieties and fluorescent moieties and $R^1$ comprises a divalent non-peptide opioid antagonist.

In accepted in vitro tests for determining binding characteristics, bis(opioid) azines corresponding to the formula $$R^1=N-N=R^1 \quad \text{(Formula XVI)}$$

have been demonstrated to be significantly longer acting than the corresponding hydrazones having the formula $$R^1=N-NH_2 \quad \text{(Formula XVII)}$$

i.e., the bis(opioid) azines are more firmly attached to opioid receptor sites and thus more difficult to remove from the sites by leaching or washing. In part this effect may be attributable to the presence of two opioid moieties in the bis(opioid) molecule, as a result of which this molecule may be able to bind to more than one receptor sites at once, thereby greatly enhancing the affinity and decreasing the rate of dissociation.

Surprisingly, however, it has been discovered that an affinity for the receptors sites even greater than that of the bis(opioid) azines is exhibited by the various hybrid compounds (most of which have a single opioid moiety per molecule) utilized in the weight gain control method of the invention. Based on in vitro tests, all of the weight control agents used in the novel method show advantageously long acting binding characteristics in conventional rat brain preparations. Especially strong binding affinity is exhibited by the thiosemicarbazones of opioid antagonists and fluorescent moieties of Formula III. These are not only very long acting with respect to the receptor sites of rat brain synaptosomal preparation but they are also long acting when bound to guinea pig ileum. Accordingly, the method of the invention is believed to provide the basis for a highly effective and superior method for the control of weight in mammals.

The mechanism by which opioid antagonists operate to control weight gain is not fully understood in the art. To some extent, the antagonist may act as an anorexic agent, i.e. an agent which suppresses appetite. Alternatively, the agent may act in some way to reduce the volume of food intake without any subjectively experienced effect on the appetite. It is also believed that opioid antagonists may affect either the metabolism of the recipient or its selection of food in a way which reduces or inhibits the gain of weight.

Regardless of the exact biological mechanism by which weight is controlled, it is believed that the biological activity of the antagonist, and thus the weight control effect achieved, depends on binding of the agent to opioid receptor sites in the mammal's system. When such agents, or other receptor probes, bind to the receptor sites, they "block" the sites, preventing or inhibiting the binding to the sites of other compositions, including endogenous opioids. It is the prevention or inhibition, i.e., the blocking, of certain such endogenous opioids from binding to the receptors which is believed to be associated with weight control. Moreover, it is believed that when such receptor probes block the receptor sites, other disorders associated with the binding of certain endogenous opioids are prevented or treated.

Specifically, it is believed that it is the delta type of opioid receptors, and the attachment of endogenous endorphins to delta-type opioid receptors that is associated with weight control. Delta-type opioid receptors and elevated levels of endogenous endorphins are also associated with various disorders, including epilepsy, schizophrenia and pre-menstrual syndrome. The probes of this invention found to be delta selective are those corresponding to Formula I, especially NAL-E.

The receptor probes of this invention, whether or not they selectively bind the delta-type opioid receptors preferentially over the other types, are effective in weight control and in treatment or prevention of disorders associated with delta-type receptors. It is believed that even the non-delta specific receptor probes of this invention are effective because such probes, while not delta-selective, still bind the delta-type opioid receptors to some significant degree. Nevertheless, the delta-selective probes are preferred because the unnecessary binding to other receptors is minimized and the high delta-affinities permits the administration of a relatively low dosage of the probe. For example, since naloxone is not delta selective or long lasting, it has been necessary to administer large doses of naloxone in an attempt to treat pre-menstrual syndrome associated with elevated endorphin levels. These abrupt doses have resulted in the suffering of withdrawal symptoms by the patient. It is believed that these withdrawal symptoms result because high naloxone doses would affect the brain, resulting in the emission of even more endorphins. Premenstrual syndrome should be treatable with relatively low doses of long lasting, delta-selective probes, thereby avoiding withdrawal symptoms. While not wishing to be bound to any particular theory, it is believed that compositions of this invention are effective in treating and preventing pre-menstrual syndrome when the composition comprises an estrogen moiety, not only because they bind to delta-type opioid receptors, but also because the estrogen moiety is carried to the central nervous system by the opioid moiety. The estrogen moiety is then believed to bind to estrogen receptors in the central nervous system, causing an excitatory effect, and thereby relieving depression associated with pre-menstrual syndrome.

Long acting binding characteristics are desirable because they prolong the effect achieved with a given dosage, tend to reduce the total intake of opiate required for weight control and treatment or prevention of other disorders associated with opioid receptors, and further tend to even out the biological impact of the administration of the weight control agent or other receptor probe.

No definitive data has been developed to explain why the compounds comprising the weight control agents or other receptor probes of the invention exhibit such persistent binding to opiate receptor sites. It is believed that upon binding, the weight control agent and/or receptor molecule undergoes some change in conformation, and that this may result in "locking" of the molecule to the site because of steric factors relating to the substantial size of the other moiety or moieties in the molecule. In this regard, it is preferred that the fluorescent or steroid moiety present in the molecule have a linear dimension of at least 15 to 16 angstroms in at least one direction. Although this criterion provides a basis for selection of weight control agents other than those specifically disclosed herein, it does not fully explain all of the advantageous properties of the weight control agents and other receptor probes of the invention, particularly the fluorescent/opioid thiosemicarbazones which exhibit superior binding to both rat brain preparation and guinea pig ileum.

Where the weight control agent or other receptor probe comprises a fluorescent moiety, it may further be used in receptor site studies as described in the copending and coassigned application of Vera Kolb Meyers, "Fluorescent Opioid Reagents and Methods of Use Thereof in the Detection of Opioid Receptors", Ser. No. 621,384, filed June 18, 1984, now U.S. Pat. No. 4,767,718. Thus, in this instance the weight control agent may be used not only therapeutically for the suppression of appetite, but also in the analysis of a patient's apparent need for weight control therapy as potentially affected by the distribution of receptor sites in the patient's system. Similarly, the receptor probes of this invention may be used other than as a weight control agent. Accordingly, the opioid receptor probes of this invention may be used not only therapeutically for the treatment or prevention of disorders associated with delta-type receptors, but also in the analysis of a patient's apparent need for therapeutic treatment of such disorders as potentially affected by the distribution of receptor sites in the patient's system.

Moreover, the fluorescent labeled moiety may be used in the evaluation of its own effectiveness in long lasting blocking of opioid receptor sites for purposes of weight control. Where a hybrid fluorescent/opioid azine, disubstituted thiourea, or thiosemicarbazone is used in vivo for diagnostic purposes or for research, it may be desirable to label it with a radioisotope as described in the aforesaid application of Vera Kolb Meyers, Ser. No. 621,384. In such application, it is particularly preferred that a fused ring fluorescent moiety be used and that it be labeled either with carbon-14, nitrogen-15 or iodine-131.

Within the above described parameters, a variety of fluorescers can constitute the fluorescent moiety. Effective long acting binding has been demonstrated with fluorescent moieties which are highly water soluble (such as for example G-orange), of modest water solubility (rhodamine), and of very low water solubility (fluorescein). Weight control agents containing any of these fluorescers are effective in accordance with the method of the invention. It may be possible that the pharmacodynamic mechanism of the weight control agent varies with water solubility. Since there are opioid receptor sites in both the brain and the gut, it may be that relatively water soluble agent, such as those containing G-orange, may work primarily by attachment to the sites in the gut, while relatively insoluble agents may more readily pass the blood/brain barrier and attach to the sites in the brain. In the former case the effect on food intake and utilization may be relatively direct, while in the latter the effect may be manifested through the central nervous system.

Solubility characteristics of the fluorescer (or other non-opioid moiety) may also have a bearing on the mode of administration of the weight control agent. Thus, an agent containing a highly soluble fluorescer such as G-orange may be advantageously administered orally, while a relatively insoluble agent might more usefully be administered parenterally or subcutaneously. However, within the skill of the art, most if not all of the various weight gain control agents should be subject to administration in more than one way. Particularly preferred fluorescers include substituted and unsubstituted fluoresceinyl and substituted and unsubstituted rhodaminyl. Especially preferred are fluoresceinyl, tetramethylrhodaminyl-B-, the residue of G-orange, and the residue of acridone. Methods for the preparation of hybrid azines and thiosemicarbazones of opioids and fluorescent moieties are described in the aforesaid application of Vera Kolb Meyers, Ser. No. 621,824.

Among the specific hybrid fluorescent/opioid antaganist compounds useful in the method of the invention are:

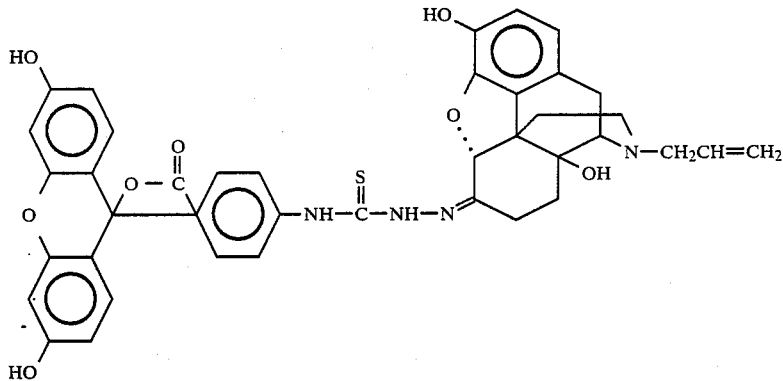
(Formula IX; 6-FN)
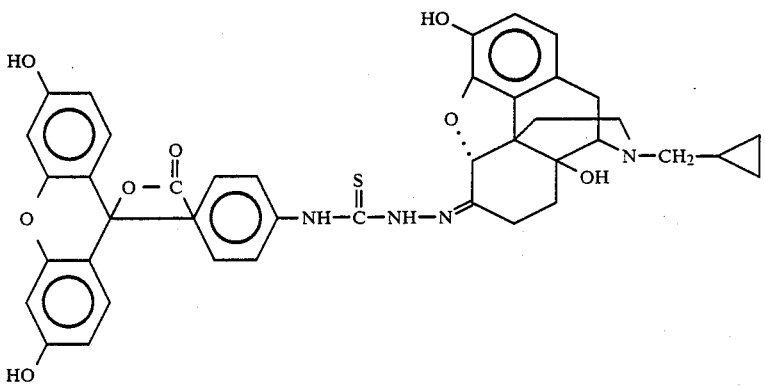
(Formula X; 6-FNX)
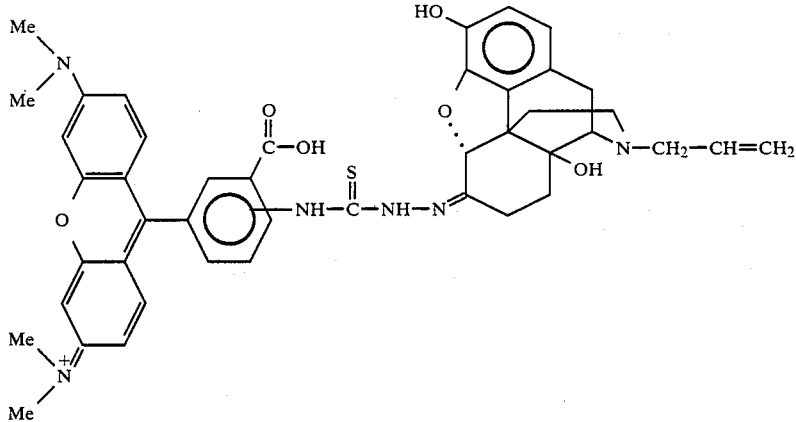
(Formula XI; 6-RN)
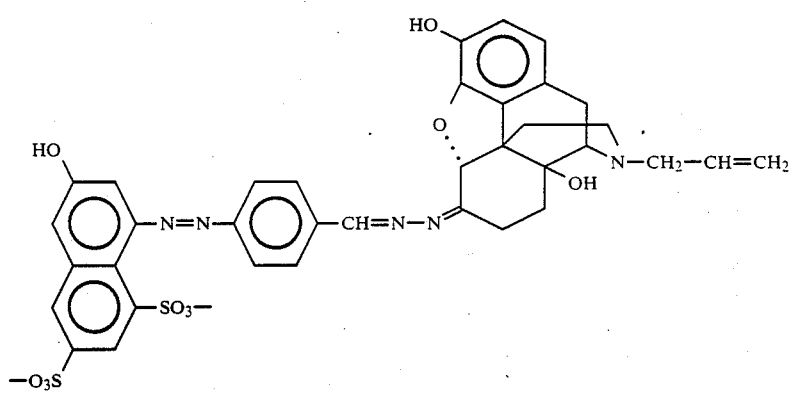
(Formula XII; NOZO)
The weight control agents or receptor probes of Formulae II and IV are novel compounds. Also novel are those compounds of Formula I which also correspond to Formula VII:

$$A^1=N-N=R^1 \qquad \text{(Formula VII)}$$

where $A^1$ is as defined above.

Where the compound comprising the weight control agent or other receptor probe contains a fluorescent moiety, it is preferably of the type preferred in the compounds of Formula III, as discussed above. Where the weight control agent or other receptor probe contains a steroid moiety, it is preferably attached to the azine nitrogen at the 3-, 6-, 11-, 16-, or 17-carbon of the steroid moiety. More preferably, it is attached at the 3-, 6-, or 17-carbon. For stability of the mixed azine, it is also preferred that there be an angular methyl group on the carbon adjacent the carbon attaching to the azine nitrogen. Suitable weight control agents or receptor probes may usefully be derived from estrone, androstene dione or other common steroids, preferably those which satisfy the criteria discussed above.

Any of the compositions of this invention are applicable to weight control and the treatment or prevention of disorders associated with opioid receptors. However, since it has been determined that weight control and certain disorders, such as epilepsy, schizophrenia and pre-menstrual syndrome, are associated specifically with delta-type opioid receptors, it is preferred that the weight control agent or other receptor probe bind selectively and preferentially with delta-type opioid receptors. Compared to non-delta specific probes, such receptor probes are more efficient since they have a higher affinity to delta receptors and risk fewer side effects since the unnecessary binding of the probes to other types of opioid receptors is reduced in favor of higher delta affinity.

Therefore, while binding of opioid receptors generally can be useful in controlling the weight of mammals and treating or preventing various disorders associated with delta-type receptors, selective and preferential binding of delta-type opioid receptors is preferred. In this respect, it has been found that compositions as set forth in Formula I, particularly NAL-E, are long lasting and selectively and preferentially bind delta-type opioid receptors.

An opioid receptor probe which selectively and preferentially binds delta-type opioid receptors also can be a useful tool for the study of the various specific types of receptors, and for the diagnosis of disorders related to the specific type of receptor. In this respect, it has been hypothesized that the disorders associated with delta-type receptors may result from an inordinate concentration of delta-type receptors in the body, and be associated with the binding of endogenous endorphins to delta-type opioid receptors.

By administering radio-labeled opioid receptor probes that bind selectively and preferentially to deltatype receptors, it is possible to locate, identify and determine the concentration of delta-type opioid receptors, and so diagnose disorders associated with such receptors. The radio-labelling of the opioid receptors may be accomplished as described in the aforesaid application of Vera Kolb Meyers, Ser. No. 621,384. In addition, administration to a mammal of such probes that are long lasting and non-toxic blocks the delta-type opioid receptors and prevent the binding of endogenous endorphins to such receptors, thereby treating or preventing disorders associated with delta-type opioid receptors.

Where the receptor probe comprises a single steroid (or fluorescent) moiety and a single nonpeptide opioid moiety as in Formula I, for example hybrid azines of estrone such s NAL-E, accepted in vitro tests on NAL-E indicate that compositions as described by Formula I have a high selectivity and preference to delta-type receptor sites. Since the tests are performed on living tissue, such tests are considered in the art to be substitutes for in vivo tests. With respect to delta site affinity, NAL-E has been found to be far more selective than naloxone in antagonizing the effects of D-Ala$^2$-Leu$^5$-enkephalin in in vitro tests on mouse vas deferens. Mouse vas deferens is rich in delta-type opioid receptors. In contrast, NAL-E has been found to be far less selective in antagonizing normorphine in in vitro tests on guinea pig ileum. Guinea pig ileum is rich in mu-type opioid receptors. Further, NAL-E has been found to produce very long lasting effects with respect to the mouse vas deferens. These findings are especially surprising as demonstrated by the fact that NAL-AD-NAL, on the other hand, has been found not to show a high delta affinity, but rather a mu receptor affinity on the order of naloxone. Due to the selective high affinity for delta sites exhibited by opioid probes corresponding to Formula I, the delta-sites can be distinguished from the other sites for selective study of delta-receptors.

No definitive data has been developed to explain why the compounds comprising the steroid-nonpeptide opioid delta-selective receptor probes of the invention exhibit such persistent selective antagonistic binding to opiate delta-receptor sites. However, while not wishing to bound to any particular theory, it is believed that the following theory may explain the phenomenon. Both NAL-E and NAL-AD-NAL are rigid, extended molecules wherein the only single bonds available for rotation are the azine linkages about which the moieties are in the anti configuration at C-6 of naloxone and C-17 of both steroids. At the C-3 position of 4-androstene-3,17-dihydrazone, the parent steroid of NAL-AD-NAL, 15% of the hydrazone is found in the syn configuration. Kolb, V. M. and Hua, D. H., "Syn-anti isomerism in the opiate hydrazones and azines derived from naloxone, naltrexone, and oxymorphone," J. Org. Chem. 49: 3824–3828 (1984). Studies with CPK space-filling models indicate that rotation is sterically hindered to about 180° in all configurations. Thus, it is possible that attachment at the C-3 position of the steroid might allow free interaction with mu-receptors, while attachment at the C-17 position, as in NAL-E, might hinder this interaction. It is possible that NAL-AD-NAL, since it is a bivalent compound, retains mu-affinity due to simultaneous binding to two proximal sites as suggested for other bivalent opioids. Coy, D. H., et al., "Increased analgesic activities of a fluorinated and a dimeric analogue of (D-Ala-2)-Methionine enkephalinamide," Biochem. Biophys. Res. Comm., 83: 977–983 (1978); Hazum, E., et al., "Increased biological activity of dimers of oxymorphone and enkephalin: possible role of receptor cross-linking," Biochem. Biophys. Res. Comm. 104: 347–353 (1982); Koman, A., et al., "Affinity probes for opioid receptors in synaptosomes. In: Investigation of Membrane-located Receptors. (Reid, E., Cook, G. M. W. and Morre, D. J., eds.)," Meth. Surv. Biochem. Anal. v. 13, pp. 497–498, Plenum, N.Y. (1984); Lipkowski, A. W., et al., "Double-enkephalins-synthesis, activity on guinea-pig ileum, and analgesic effect," Peptides 3: 697–700 (1982); Portoghese, P. S., et al., "Opioid agonist and antagonist bivalent ligands as receptor probes," Life Sci. 31: 1283–1286 (1982);

Shimohigashi, Y., et al., "Dimeric tetrapeptide enkephalins display extraordinary selectivity for the delta-opiate receptor," Nature 297: 333–335 (1982).

A hybrid azine of estrone has one opiate unit. Thus, for example, the mixed azine of naloxone and estrone corresponds to the formula:

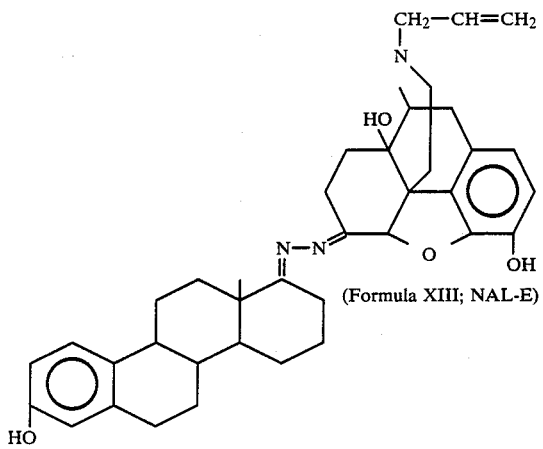

(Formula XIII; NAL-E)

A mixed azine of a dione such as androstene dione has two opiate units and may be thought of as a bis(opioid azine) with a long rigid spacer moiety between the two opioid units. Thus the mixed azine of naloxone and androstene dione has the structure:

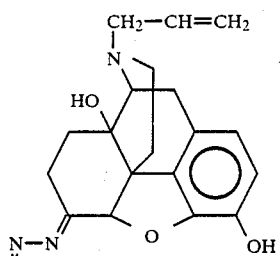

(Formula XIV; NAL-AD-NAL)

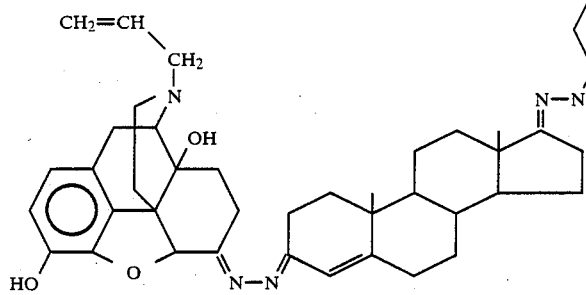

The mixed azines of Formula VII may be prepared by reacting an opioid antagonist free base with a hydrazine of the steroid. To carry out the reaction, a concentrated solution of the steroid hydrazone may be prepared and the free base of the opioid antagonist added to the solution. The progress of the resulting reaction may be followed using conventional analytical techniques, for example, thin layer chromatography. After the reaction is substantially complete, the reaction mixture is preferably quenched with $H_2O$, after which solid product obtained may be recovered by filtration and dried. Steric and kinetic factors favor the formation of the anti-anti isomer in this synthesis. A similar method may be used to prepare the mixed diazine of an opioid antagonist and a steroid dione, such as androstene-3,17-dione, except that in the latter case the free base of the opioid is reacted with the corresponding dihydrazone of the steroid.

The novel N,N'-disubstituted thioureas of Formula IV may be prepared by reaction of a fluorescent substituted isothiocyanate with an amino substituted, typically a 6-amino substituted, opioid antagonist. Either an alpha amine or beta amine can be used. In the synthesis, the amine substituted opioid may be dissolved in a suitable solvent such as triethylamine, the isothiocyanate of the fluorescer dissolved in a solvent such as a lower alcohol, and the two solutions mixed and reacted at moderate temperature, for example, room temperature, for a time sufficient for condensation of the amine and isothiocyanate groups. Again, the progress of the reaction may conveniently be followed by thin layer chromatography. After the reaction is complete, the product may be recovered by concentrating the reaction mixture, followed by crystallization. Addition of a lower alcohol may promote the crystallization.

Novel preparations for control of weight or treatment or prevention of disorders associated with opioid receptors are provided by combining the weight control agent or other receptor probe with other materials which facilitate its administration to a mammal. Thus, for example, where oral administration is contemplated, the weight control agent or other receptor probe may be mixed with pharmaceutically acceptable excipients and/or adjuvants. Where parenteral or subcutaneous administration is desired, the weight gain inhibiting agent or other receptor probe may be formulated with a suitable pharmaceutically acceptable carrier. Dosage amounts and concentrations of particular components may be readily determined by those skilled in the art.

To carry out the novel weight control method of the invention, an effective amount of the weight control agent is administered to the mammal in any convenient manner, but preferably orally. Upon ingestion, injection, or absorption, the agent attaches to the opioid receptor sites in the gut or brain and blocks them, resulting in inhibition of weight gain. In most instances, administration of an appropriate amount of the weight control agent will result in an actual loss of weight. Because the weight control agents used in the method of the invention are long lasting, effective control of weight can be realized by the administration of modest amounts of the agent at relatively infrequent intervals. A persistent and even effect is thus achieved with minimal toxicity or other adverse side effects.

The novel method of the invention for treating or preventing disorders associated with delta-type opioid receptors, and/or elevated levels of endorphins, is carried out substantially as described with respect to weight control.

Similarly, for locating, identifying and determining the concentration of delta-type opioid receptors, or for diagnosing disorders associated with delta-type opioid receptors, an effective amount of the radio-labeled delta-selective opioid receptor probe is administered to the mammal in any convenient manner, but preferably orally. Upon ingestion, injection, or absorption, the agent or other probe attaches to the opioid receptor sites in the gut or brain and blocks them. The radiation pattern formed thereby is then observed.

In the in vitro procedures, a tissue sample, which may be from a biopsy, is stained by contacting it with the labeled opioid receptor probe in the manner generally described above. The probe is labeled either by radio-labeling or by the presence of a fluorescent moiety. The emission pattern formed thereby is then observed. The concentration of the labeled probe indicates the location and concentration of receptors to which they bind.

Comparative analysis may be conducted by competitive binding assays. Unknown levels of binding sites can be determined by incubating a sample with specified known concentrations of fluorescent labeled or radio-labeled reagent and non-fluorescent labeled opioid, and comparing the resulting emission intensity or fluorescence polarization with that observed upon incubating various known concentrations of receptors with the same concentrations of fluorescent and non-fluorescent opioids.

The following examples illustrate the invention.

EXAMPLE 1

Synthesis of 1-(N)-Fluoresceinyl Naloxone Thiosemicarbazone ("6-FN")

Naloxone hydrazone (0.114 grams; 0.333 millimoles) was added to a solution of fluorescein isothiocyanate (0.1351 gram; 0.347 millimoles; Sigma Chemical, St. Louis, isomer I) in tetrahydrofuran (2 ml.; Fisher Certified) and ethyl alcohol (4 ml.; 100%, histological quality). The resulting solution was stirred at room temperature until the reaction mixture contained no more naloxone hydrazone as indicated by a thin layer chromatography (TLC). The container was wrapped in aluminum foil. Thereafter, portions of ethyl alcohol and water were added to the reaction mixture. Orange crystals formed which were filtered off and dried. The structure of the crystals was determined to be that of 1-(N)-fluoresceinyl naloxone thiosemicarbazone ("6-FN") based on spectroscopic evidence and elemental analysis. Major physical and spectral characteristics of 6-FN included: Mp>300°. IR (nujol): $\nu$1740 (C=C), 1635, 1590, 1500, 1325, 1268, 1208, 1182, 1110, 1028, 993, 952, 912, 852, 808, 722, 618 cm$^{-1}$. $^1$H-NMR (100 MHz) (DMSO-d$_6$):$\delta$8.442 (1H, d, J~2 Hz), $\delta$8.034 (1H, split d, J~8 Hz, J~2 Hz), 7.251 (1H, d, J~8 Hz) (protons from the non-phenolic aromatic ring of the fluorescein moiety); 6.678, 6.602, 6.583 (8 H's, single peaks) (aromatic protons from the phenol rings of the fluorescein and naloxone moieties); 6.11–5.10 (complex signal, vinylic H's of the allyl group); 5.029 (1H, s, bridgehead H at C-5) ppm; the upfield peaks look like those of naloxone. C,H,N,S analysis: calculated: C, 65.74; H, 4.69; N, 7.67; S, 4.39. Found: C, 65.81; H, 4.64; N, 7.64; S, 4.34. Fluorescence properties of 6-FN: (a) A $10^{-6}$ M solution in pH 7 phosphate buffer showed an excitation maximum at 493 nm and an emission maximum at 513 nm, as compared to 493 nm and 510–511 nm, respectively, for free fluorescein; (b) Absorption maximum $10^{-5}$ M solution (phosphate buffer) was at 493 nm (A=0.410; c) Quantum yield of 6 FN compared to free fluorescein was about 67% at $10^{-9}$ M; d) fluorescence polarization was 0.038 for 6-FN and 0.022 for free fluorescein.

EXAMPLE 2

Preparation of 1-(N)-tetramethylrhodaminyl-B-naloxone Thiosemicarbazone ("6RN")

Tetramethylrhodaminyl-B-isothiocyanate (Sigma, St. Louis; 10 mg.; 2.255×10−5 mol) was almost completely dissolved in a mixture of tetrahydrofuran and ethyl alcohol (approximately 3 cc), producing a wine-red solution. To this solution was added naloxazone, i.e., naloxone hydrazone, (8.5 mg.; 2.49×10−5 mol). After the naloxazone was added, the solution changed from wine-red to a brownish color and became cloudy. After 33 minutes of reaction, a sample of the reaction solution was removed and subjected to thin-layer chromatographic analysis. The results of this analysis did not indicate the presence of any remaining naloxazone. Approximately one hour after the addition of naloxazone, the reaction mixture was quenched by addition of water. Upon quenching, the solution warmed slightly, but no precipitate formed. Thereafter, the solution was concentrated to approximately its initial volume by removal of solvent on a rotary evaporator under mild heating. Significant foaming was observed during the concentration of the solution, and a precipitate formed which was separated by filtration. Thereafter, the mother liquor was subjected to further evaporation to one quarter of the original volume, upon which additional precipitation occurred, producing a second crop of crystals which was also removed by filtration. Both crops of crystals were dried in a vacuum oven. The product was 1-(N)-tetrame-thylrhodaminyl-B-naloxone thiosemicarbazone.

EXAMPLE 3

Synthesis of 1-(N)-Fluorosceinyl Naltrexone Thiosemicarbazone ("6-FNX")

Naltrexazone (0.0573 grams; 1.61×10−4 mol) was dissolved in a minimum amount of tetrahydrofuran and the resulting solution added (together with ethyl alcohol rinsings from the container in which the dissolution was carried out) to a stirred solution of fluorosceinyl isothiocyanate (Sigma Chemical Co., Isomer I; 0.0641 grams; 1.65×10−4 mol) in THF (1 cc; Fisher, certified) and ethyl alcohol (2 cc). As soon as the naltrexazone was added, the color of the fluoresceinyl isothiocynate solution began changing from red to orange. Reaction was carried out under agitation at room temperature while the reaction solution was protected from light with aluminum foil. After approximately one hour and 5 minutes of reaction, a small quantity of precipitate was formed and a sample taken for TLC analysis. Thereafter, additional ethyl alcohol was added until further precipitation was obtained. After one hour and 35 minutes the reaction was stopped by filtering out the solid precipitate. The solid product was washed twice with ethyl alcohol, yielding a crystallizate of 1-(N)-fluoresceinyl naltrexone thiosemicarbazone ("6-FNX")

(0.0223 grams), determined by TLC analysis to be substantially pure.

Further crystallization from the mother liquor yielded an additional quantity of 6-FNX (0.0182 grams). By adding water to the remaining mother liquor, a third crop of crystalline 6-FNX was obtained (0.0410 grams). The third crop was washed with ethyl alcohol and water. Overall yield at this point was 67.9%. Further crystallization from the mother liquor provided a fourth crop of 6-FNX crystals (0.0138 grams) bringing the total yield to 79.4%.

EXAMPLE 4

1-(N)-fluoresceinyl benzophenone thiosemicarbazone ("6-FB") was synthesized in a manner comparable to the methods described in Examples 1–4.

The opioid receptor binding characteristics of 6-FN, 6-FNX, 1-(N)-fluoresceinyl oxymorphone thiosemicarbazone ("6-OF)", 6-FB, and 6-RN were assessed by their effectiveness in displacing dihydromorphine ($^3$H-DHM) from rat brain synaptosomal plasma membranes. In this assessment, radiolabeled $^3$H-DHM ($^3$H-DHM*) was initially bound to the receptor sites on the membranes, following which the membranes were contacted with solutions of the fluorescent-labeled reagent. After removal of the reagent solution, the membranes were washed for removal of any displaced $^3$H-DHM*. Radioactivity counting both before and after treatment with the fluorescent reagent gave an indication of displacement of $^3$H-DHM*.

All of the fluorescent-labeled compounds except 6-FB were found effective for displacement of $^3$H-DHM*. Increasing concentrations of the fluorescent reagents were effective for progressive displacement of the indicator ligand. Generally, the fluorescent reagents were not as effective as their parent opioids as competitors for displacement of $^3$H-DHM*. However, 6-FN, 6-FNX, 6-OF and 6-RN showed sufficient binding activity for use in the detection and quantification of receptor sites in the synaptosomal membranes. The following IC$_{50}$ values (concentrations necessary for 50% displacement of $^3$H-DHM*) were determined graphically: naloxone 0.9 nM; 6-FN 20 nM, 6-RN 12 nM; naltrexone 0.3 nM; 6-FNX 5 nM; 6-FO 20 nM. The control compound 6-FB was inactive at $10^{-6}$ M. The Hill coefficients were: naloxone 1.09; 6-FN 0.671; 6-RN 1.09; naltrexone 1.15; 6-FNX 0.675; 6-FO 0.989.

In order to investigate the anomalous displacement curve of 6-FN, this reagent was also subjected to the site selectivity analysis technique described by Terenius and Wahlstrom, *European Journal of Pharmacology*, Vol. 40, pp. 241–248 (1976). In this analysis, $^3$H-DHM and $^3$H-D-Ala$^2$-[Leu]enkephalin ($^3$H-DALE) were used as indicator ligands. To provide a comparison of site selectivity, the non-peptide antagonist compound was tested for displacement of labeled opioid from a substrate which had been previously contacted with an indicator ligand solution containing DHM*(0.43 nM) and cold DALE (0.43 nM). These results were compared with the displacement obtained from a substrate which had been contacted wit an indicator ligand solution containing cold DHM (0.43 nM) and DALE* (0.43 nM). FIG. 1 is a plot of percent bound DALE* as obtained from the second displacement test versus percent bound DHM* from the first displacement test for a series of antagonist compound solutions of varying strength. In FIG. 1 it will be noted that compounds which displace the two indicator ligands differently provide a curve which is convex towards the axis of the labeled indicator ligand which is less favorably displaced. The results of this test show clearly the difference between 6-FN and naloxone with respect to site selectivity. The IC50 values determined graphically from this test were: (a) with $^3$H-DHM; naloxone 1.3 nM; 6-FN 12 nM; (b) with $^3$H-DALE; naloxone 20 nM; 6-FN 17 nM.

EXAMPLE 5

6-FN was tested for activity on an electrically stimulated guinea pig ileum longitudinal muscle preparation. In this test, a specimen of guinea pig ileum was stretched between two wires in a nutrient solution (2.5 mil.) and stimulated supramaximally at 0.1 Hz. In the absence of opioid agonists and antagonists electrical stimulation of the muscle results in contraction.

Figure 2:
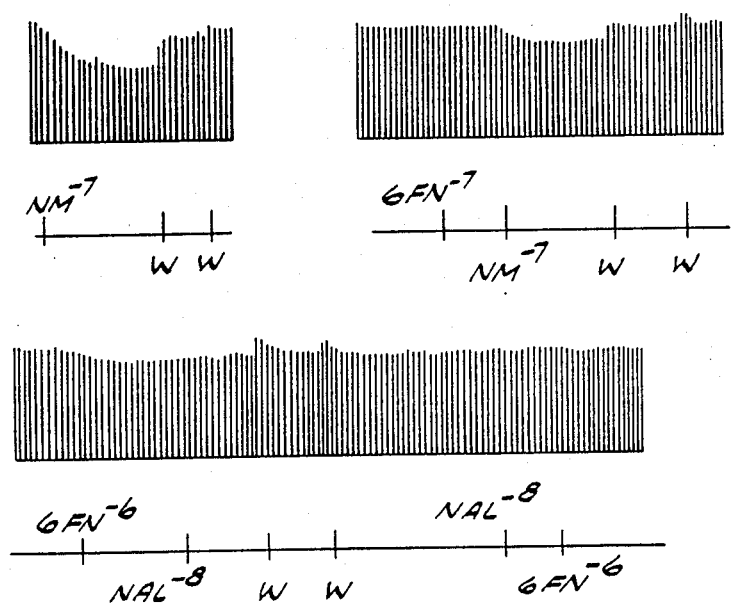
FIG. 2 illustrates the agonist effect of normorphine in inhibiting the contraction of guinea pig ileum; the antagonist effect of 6-FN with respect to normorphine; the slight agonist effect of 6-FN; and the antagonist effect of naloxone with respect to 6-FN as reported in Example 5.

Addition of an aqueous solution of normorphine (25 microliters; $10^{-7}$ M) substantially inhibited contraction of the muscle (FIG. 2). Introduction of an aqueous solution of 6-FN ($10^{-6}$ M in 10% ethanol; 25 microliters) into the nutrient solution (final 6-FN concentration: $10^{-7}$ M) prior to the introduction of normorphine significantly inhibited the agonist effect of normorphine, though the effect was ten times less effective than the inhibiting effect achieved with naloxone. Washing of the ileum specimen did not readily eliminate the antagonist effect. In this respect 6-FN was similar to naloxone.

As illustrated in FIG. 2, $10^{-6}$ M 6-FN exhibited a partial agonist activity which was observed to be reversible with $10^{-7}$ M naloxone.

EXAMPLE 6

Synthesis of the Mixed Azine of Oxymorphazone and G-Orange ("OZO")

G-orange (Fluka; 76.3 mg; 0.1588 mmol) was dissolved almost completely in a mixture of water and ethanol. The G-orange was first mixed with the water (1.2 ml) after which the ethanol (0.7 ml) was added to the mixture. A solution of oxymorphazone (50.6 mg; 0.1606 mmol) in ethanol (200 l) and a minor amount of water was prepared and added to the G-orange solution. Inclusion of a minor fraction of ethanol in the aqueous solution of G-orange, and a minor fraction of water in ethanolic solution of oxymorphazone, prevented the formation of a precipitate that might otherwise have been produced on contact of the two solutions. The mixed solution of G-orange and oxymorphazone was stirred at room temperature in the dark for 7½ hours, during which time the progress of the reaction was followed by thin layer chromotography (TLC). After 7½ hours, some solid was observed to have been formed in the flask. Additional ethanol was thereafter added to the reaction solution and the solid filtered off. The solid product was dark purple in color and was insoluble in ethanol but soluble in water. Upon evaporation of the reaction solution mother liquor, additional solid precipitated. A crude solid product obtained was analyzed for purity by both TLC and HPLC. Both methods indicated a complete absence of oxymorphazone in the product, and only a trace of G-orange.

Two solvent systems were used for TLC, the $R_f$ values for which are indicated in Table 1. The TLC was carried out on E. Merck aluminum supported sheets (precoated TLC sheets, silica gel 60F-254, layer thickness 0.2 mm, catalogue no. 5539). The two eluents used were: System 1: chloroform: methanol: concentrated ammonium hydroxide=135:10:2 (v/v), and System II: ethanol: acetic acid: water=60:30:10 (v/v). The spots were observed in UV—254 nm; 366 nm for the fluorescent compounds. The latter were also observed in visible light.

The HPLC peak positions are given in Table 2. These analyses were done on a Laboratory Data Control instrument equipped with a C-18 bondapack analytical column from Waters. The solvent used for the HPLC was acrylonitrile 0 to 80% gradient, 0.1% ammonium acetate (pH about 5.9).

TABLE 1

| Compound | $R_f$ Values System I $R_f$ | System II $R_f$ | Comment |
|---|---|---|---|
| oxymorphazone | 0.32 | 0.07 | spot observed in UV (254 nm) |
| G-orange | 0 | 0.59 | orange spot (vis. light) |
| OZO | 0 | 0 | purple spot (vis. light) |

TABLE 2

| Peak positions in HPLC [mm] | | |
|---|---|---|
| oxymorphazone | 23.2 (syn) | 20.0 (anti) |
| G-orange | 26.5 | |
| OZO | 34.5 | |

EXAMPLE 7

Synthesis of the Mixed Azine of Naloxone and G-Orange ("NOZO")

G-orange (Fluka; 20.0 mg; 0.0416 mmol) and naloxazone (14.1 mg; 0.0414 mmol) were reacted in a manner analogous to that described in Example 6 for the synthesis of the mixed azine of oxymorphone and G-orange. The TLC and HPLC behavior was closely analogous to that reflected in the data of Table 1 and 2 for the reaction with oxymorphazone. $R_f$ values for NOZO in both systems 1 and 2 were zero. The HPLC peak position was at 34.0 mm but another small peak at 37.1 mm was also present. This small peak probably indicates the presence of an isomer of the azine (three isomers being possible: anti-anti, anti-syn, and syn-syn).

Neither G-orange nor naloxazone were present in the NOZO product as detected by either TLC or HPLC.

EXAMPLE 8

Synthesis of fluorescein labeled 6-δ- aminonaloxone [N-(1-N-allyl-14-hydroxynordihydro-6δ-morphinanyl)- N'-fluoresceinyl thiourea;"FAN"]

6δ-amino naloxone dihydrochloride (22.0 mg; 0.0549 mmol) was dissolved in triethylamine (300 μl). Fluorescein isothiocyanate (Sigma; isomer 1; 24.4 mg; 0.0627 mmol) was dissolved in ethanol (200 μl) and triethylamine (20 μl). The two solutions were thereafter mixed and maintained at room temperature in the dark (wrapped in aluminum foil) for two hours, during which a condensation reaction occurred between the amine and isothiocyanate. The progress of the reaction was followed by TLC. After two hours, a portion of water was added to the reaction mixture and the mixture then concentrated by vaporation on a rotary evaporator. A portion of ethanol was added and crystallization resulted, producing orange crystals. Additional crystals were obtained by cooling the mother liquor. As indicated by both TLC and HPLC analysis, the product was substantially pure N-(1-N-allyl-14-hydroxynordihydro-667 -morphinanyl)-N'-fluoresceinyl-thiourea.. TLC and HPLC data is set forth in Table 3.

TABLE III

| Compound | $R_f$ Values System I $R_f$ | System II $R_f$ | Comment |
|---|---|---|---|
| 6δ -amino naloxone | 0.045 | 0.31 | spot observed in UV (254 nm) |
| FITC + Et$_3$N + HCl | 0 | 0.81 | orange spot |
| FAN | 0 | 0.58 | orange spot |

Using the method of Example 4, various weight control agents of the invention were tested for displacement of $^3$H-dihydromorphine from opioid receptors in rat brain membrane preparations. For purposes of comparison, the displacement tests were also run on naloxone ("NAL"), naltrexone ("NALT") and oxymorphone ("OXY"), and the mixed azine of oxymorphone and G-orange ("OZO"). The data was analyzed, using the program LIGAND of Munson and Rodbard. The results of these displacement test are summarized in Table 4.

TABLE IV

| COMP | Kd nM | % STD. ERROR | MEANSQ. | SUMSQ. |
|---|---|---|---|---|
| DHM | 3.1 | 10.9 | 3.13 | 42.3 |
| NAL | 1.6 | 16.4 | 4.44 | 38.9 |
| 6-FN | 11.5 | 11.5 | 1.44 | 18.0 |
| 6-RN | 5.3 | 14.7 | 2.91 | 34.2 |
| 6-FAN | 18.9 | 16.6 | 1.41 | 16.5 |
| NAZO | 120.5 | 14.5 | 1.35 | 15.9 |
| OXY | 1.1 | 18.4 | 1.22 | 10.7 |
| 6-FO | 12.8 | 16.7 | 0.94 | 11.0 |
| OZO | 37.0 | 16.3 | 5.09 | 59.8 |
| NALT | 0.4 | 15.2 | 0.81 | 6.1 |
| 6-FNX | 2.6 | 16.9 | 4.93 | 52.5 |

EXAMPLE 10

Figure 3:
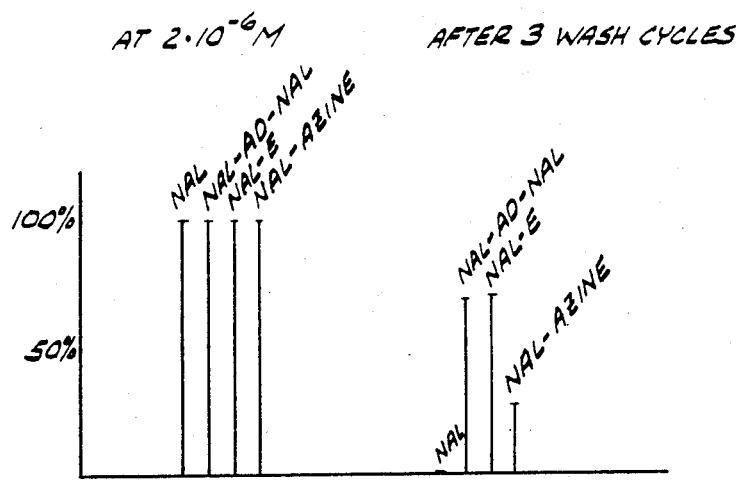
FIG. 3 is a bar graph illustrating the relative persistence of binding of naloxone and certain of the weight control agents of the invention to the opiate receptors in rat brain cells in 50 mM Tris-HCl pH 7.5 buffer, as determined by the effect on inhibition of $^3$H-dihydromorphine ($^3$H-DHM) binding which results from repetitive washing of a rat brain preparation to which the opioid had been attached.

To determine the persistance of binding of certain weight control agents of the invention to opioid receptor sites, the extent of dissociation of the opioid from the receptor site effected by washing was determined in accordance with the method described by E. H. Hahn et al., *J.Neuroscience*, 2, p. 572 (1982). Inhibition of the binding of 3H-DHM by the weight control agent was determined both prior to washing and after three wash cycles. The tests were conducted in 50 nM Tris HCl pH 7.5 buffer. The results of these tests are set forth in FIG. 3.

Figure 4:
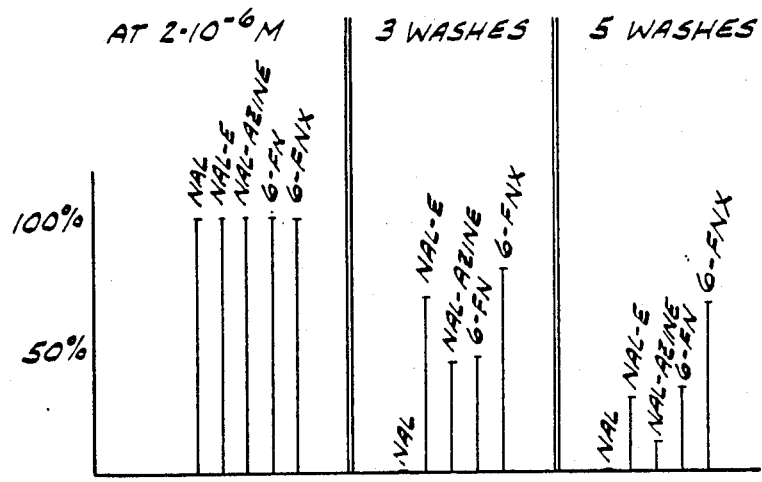
FIG. 4 is a bar graph similar to FIG. 2 for $^3$H-DHM displacement tests carried out in HEPES buffer.

Similar tests were run in HEPES buffer and the effect on $^3$H-DHM displacement determined before washing, after three washes, and after five washes. The results are set forth in FIG. 4.

EXAMPLE 11

Synthesis Of A Mixed Azine Of Estrone And Naloxone ("NAL-E").

The mixed azine was prepared by reacting naloxone free base with estrone hydrazone in a one-to-one molar ratio. To prepare the free base, naloxone hydrochloride (Endo) was dissolved in water and poured into a separatory funnel containing dilute borax solution and chloroform. The resulting mixture was extracted three times with chloroform. The combined chloroform extracts were dried and evaporated, giving the naloxone free base as a white crystalline solid in 100% yield.

Estrone hydrazone was prepared in the manner described by Dandliker et al., *Cancer Research*, Vol. 38, p. 4212 (1978). Estrone hydrazone was crystallized out of the reaction mixture (melting point greater than 270° C.). Its $^{13}$C-NMR revealed only one (anti) isomer at the 17-carbon.

Estrone hydrazone (0.0757 g., $2.66 \times 10^{-4}$ mol) was dissolved in boiling ethanol (5 ml; 100%). To this hot solution naloxone free base (0.0881 gr., $2.69 \times 10^{-4}$ mol) was added, and the resulting mixture was boiled briefly and then left to stir at room temperature in the dark. The progress of the reaction was followed by TLC, using two different methods for detection of spots: observing them under UV light; and observing the color development after the TLC plate was sprayed with 50% sulfuric acid solution and heated to over 100° C. Naloxone shows up very strongly in the UV, while estrone hydrazone shows up only faintly. The product mixed azine, which has a higher $R_f$ value than either naloxone or estrone hydrazone, shows up very strongly in the UV. By using the color development method, estrone hydrazone (red) and the mixed azine product (orange) can be detected very easily, while naloxone does not show up at all. After only traces of naloxone and estrone hydrazone could be detected by TLC, the reaction was quenched by pouring the reaction solution into ice. The white solid thus formed was filtered off and dried in a vacuum oven, giving 0.1303 g (82.3% yield) of the mixed azine of estrone and naloxone (melting point greater than 120° C. Dec.). The product was recrystallized from chloroform and gave a satisfactory C, H, N analysis. Its IR, $^1$H NMR and $^{13}$C-NMR were in agreement with the proposed structure. The $^{13}$C-NMR revealed that the azine bond is configurationally pure, i.e., anti-anti. The MS (electron impact) did not give the parent peak as opposed to, for example, the hydrazones of naloxone, naltrexone and oxymorphone.

EXAMPLE 12

NAL-E and NAL-AD-NAL were tested on the brain membranes of male Sprague-Dawley rats (each rat being 200–300 gms.), the vas deferens of male NMRI (A-Lab, Solna, Sweden) mice (each mouse being 25–30 gms.), and the ileum myenteric plexus-longitudinal muscle of male pigmented guinea pigs (each guinea pig being 300–500 gms.). The "single dose" method of Kosterlitz, H. W. and Watt, A. J., "Kinetic parameters of narcotic agonists and antagonists, with particular reference to N-allylnoroxymorphone (naloxone)," Br. J. Pharmac. Chemother. 33: 266–276 (1968) was used.

Each of several samples of mouse vas deferens (m.v.d.) and guinea-pig iluem myenteric plexus-longitudinal muscle (G.p.i.) was placed in a bath fluid comprising Krebs solution at 35° C. (for vas deferens the preparations excluded $Mg^{+2}$) and continuously aerated with 95% oxygen and 5% carbon dioxide. The pH of the baths was 7.4. The preparations were stimulated with supramaximal rectangular electrical impulses of 60–80 V and one msec duration at 0.1 Hz to induce contractions in the m.v.d. and G.p.i. samples. Contractions were measured isometrically with a Grass FT03 transducer and a Grass 79 EEG and Polygraph recorder. According to the standard experimental sequence of the "single dose" method, first a dose-response curve was constructed for an agonist (normorphine was employed as an agonist in G.p.i. and D-Ala$^2$-Leu$^5$-enkephalin (DALE) was used as an agonist in m.v.d.). The curve was produced by measuring the degree of tissue contraction induced by electrical stimulation of tissue suspended in a bath with a given dose of agonist. The procedure is repeated for seven other doses, and the resulting measurements are plotted against the dosages. Twenty minutes after the last agonist dose, in separate trials each of the test compounds, NAL-E, NAL-AD-NAL, naloxone, 17-beta-estradiol and the steroidal parents of NAL-E and NAL-AD-NAL, namely estrone hydrazone (EH) and $\Delta^4$androstenedione-(3,17)-dihydrazone (ADDH), was incubated for twenty minutes and a high dose of agonist was added to achieve a combined effect of agonist and the test compound. Then the preparations were washed and the recovery of the m.v.d. or G.p.i. from the agonist effects was assayed at 10–20 minute time intervals.

The NAL-E and NAL-AD-NAL were tested at doses ranging from 25–1000 nM and were found to inhibit DALE-induced contractions of the m.v.d. by 20–50% at all doses tested. These NAL-E and NAL-AD-NAL induced antagonisms in the m.v.d. were not reversed by addition of naloxone, even at a naloxone dosage of 10,000 nM. (Nor were the NAL-E or NAL-AD-NAL antagonisms in the G.p.i. reversed by naloxone.) While 17-beta-estradiol had no inhibitory effect on the contractions, the NAL-E and NAL-AD-NAL parent hydrazones, EH and ADDH, produced inhibitory effects of magnitudes similar to NAL-E and NAL-AD-NAL. However, none of the steroids, EH, ADDH or 17-beta-estradiol, showed opioid antagonism in either the m.v.d. or G.p.i. bioassay. In the G.p.i., both naloxone derivatives, NAL-E and N-ADDH-N, were somewhat longer acting than their parent opioids. As shown in the table, NAL-E antagonism was very longlasting in the m.v.d.

The antagonism by test compounds of the agonist effects observed in the m.v.d. and G.p.i. bioassays are shown in the table below as the dissociation constant ($K_e$) and the half-times of recovery ($t_{\frac{1}{2}}$). The dissociation constant, $K_e$, is determined at the apparent equilibrium by dividing the concentration of the test compound by the dose ratio for the test compound at the apparent equilibrium. The dose ratio (DR) is the ratio of the agonist concentrations necessary to produce identical effects in the presence of the antagonist test compound as in the absence of the antagonist, and is calculated as follows: $DR = M_3/(M_2 - M_1)$. $M_1$ is the equivalent dose of normorphine which gives an agonist effect identical to that of the test compound, and is determined by extrapolating from the normorphine dose-response curve. $M_2$ is the equivalent dose of normorphine which gives an agonist effect identical to that of a combined dose of the test compound and normorphine, and is determined by extrapolating from the normorphine dose-response curve. $M_3$ is the concentration of normorphine added in combined dose with the test compound. The results obtained for naloxone were in close agreement with the study described in Magnan, J., et al., "The binding spectrum of narcotic analgesic drugs with different agonist and antagonist properties," Naunyn-Schmiedeberg's Arch. Pharmacol. 319: 197–205 (1982).

| Compound | MOUSE VAS DEFERENS K$_e$(nM) | t$_{\frac{1}{2}}$(min) | GUINEA-PIG M. PLEXUS K$_e$(nM) | t$_{\frac{1}{2}}$(min) |
|---|---|---|---|---|
| Naloxone* | 51.0 (43–59) | 10 (4–21) | 3.1 (2.6–3.7) | 15 (10–21) |
| NAL-E** | 5.8 (3.8–8.8) | 1000+ | 69.0 (59–93) | 27 (7–94) |
| NAL-AD-NAL* | 37.0 (29–47) | 19 (14–24) | 5.7 (2.5–13) | 34 (15–79) |

K$_e$ and t$_{\frac{1}{2}}$ are given in geometric means followed, in parentheses, by 95% confidence limits. The effects of NAL-E on m.v.d. were almost irreversible in some observations.
*There were four observations of the effects on m.v.d., and five observations of the effects on G.p.i.
**There were five observations of the effects on m.v.d., and five observations of the effects on G.p.i.

EXAMPLE 13

Rat brain membranes were prepared and binding assays performed as previously described by Neil, A. in "Detection and characterization of four opioid binding sites in the mouse brain," Acta Pharmacol. Tox. 56: 108–116 (1985). Mu-site affinity (i.e., affinity to mu-receptors) was assayed using 0.2 nM [$^3$H]-dihydromorphine ([$^3$H]-DHM), delta-site affinity was assayed using 1 nM [$^3$H]-D-Ala$^2$-Leu$^5$-enkephalin ([$^3$H]-DALE) with 30 nM Tyr-D-Ala-Gly-MePhe-Gly-ol (DAGO) added to suppress mu-binding, and kappa-site affinity was assayed using 1 nM [$^3$H]-($\pm$)-Ethylketocyclazocine ([$^3$H]-($\pm$)-EKC) with 200nM each of DAGO and D-Ala$^2$-D-Leu$^5$-enkephalin (DADL) added to suppress mu and delta-binding, respectively. Note that only ($-$)-EKC binds at the concentration reported for the ($+$)-EKC. Dissociation constants (K$_i$) were then calculated from observed 50 per cent inhibition (IC$_{50}$) in accordance with the procedures described by Cheng, Y. C. and Prusoff, W. H. in "Relationship between the inhibition constant (K$_i$) and the concentration of inhibitor which causes 50 per cent inhibition IC$_{50}$) of an enzymatic reaction," Biochem. Pharmacol. 22: 3099–3108 (1973).

The affinities of the test compounds for delta-, mu- and kappa-type opioid binding sites determined in binding assays designed for studying site selectivity are shown in the following table.

| Compound | INHIBITION OF BINDING K$_i$(nM) Delta | Mu | Kappa | AFFINITY K$_i^{-1}$ (nM$^{-1}$) Delta | Mu | Kappa | RELATIVE AFFINITY Delta | Mu | Kappa |
|---|---|---|---|---|---|---|---|---|---|
| Naloxone | 29.0 | 1.7 | 18 | 0.034 | 0.590 | 0.056 | 5 | 87 | 8 |
| NAL-E | 3.9 | 17.0 | 19 | 0.260 | 0.058 | 0.053 | 70 | 16 | 14 |
| NAL-AD-NAL | 8.5 | 1.6 | 18 | 0.120 | 0.630 | 0.056 | 5 | 78 | 7 |

Relative affinity for a site is the K$_i^{-1}$ value for that site multiplied by 100 and divided by the sum of the K$_i^{-1}$ values.

The relative potencies of the compounds as antagonists in the bioassays of Example 12 and as inhibitors at the delta and mu binding sites in the binding assays of Example 13 are shown in the table below. The table indicates that NAL-E was the most potent antagonist of DALE effects on the m.v.d. (rich in delta sites), nine-fold more potent than naloxone. Further, the table indicates that NAL-E was 22-fold less potent than naloxone in the G.p.i. (rich in mu sites).

The figures given in the table for the bioassays are the ratio of the K$_e$ found in Example 12 for naloxone to the K$_e$ found for the indicated compound, thereby showing the selectivity, relative to naloxone, of the indicated compound for the sites of the m.v.d. (delta), and G.p.i. (mu). The column marked m.v.d./G.p.i. shows the relative affinity of the indicated compound for the sites of the m.v.d. (delta) compared to the affinity of the compound for the sites of the G.p.i. (mu). The figures given in the table for the binding assays are the ratio of the K$_i$ found in Example 13 for naloxone with respect to mu sites to the K$_i$ found for the indicated compound with respect to the indicated sites, thereby showing the selectivity, relative to naloxone, of the indicated compound for the indicated types of sites. Nal-E is shown to be far more delta selective than naloxone.

| Compound | BIOASSAYS M.V.D. | G.P.I. | M.V.D. G.P.I. | BINDING ASSAYS Delta | Mu | Kappa |
|---|---|---|---|---|---|---|
| Naloxone | 1.0 | 16.0 | 0.063 | 1.0 | 17.0 | 0.059 |
| NAL-E | 8.8 | 0.74 | 12.0 | 7.4 | 1.7 | 4.4 |
| NAL-AD-NAL | 1.4 | 8.9 | 0.16 | 3.4 | 18.0 | 0.19 |

Relative potencies in bioassays are given with the K$_e$ value of naloxone in the M.v.d. taken to be 1. Relative potencies in binding assays are given with the K$_1$ value of naloxone in inhibiting $^3$H-DALE taken to be 1.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. A method for locating, identifying or determining the concentration of delta-type opioid receptors in a sample of tissue, cells, or subcellular particles, comprising the steps of:
   contacting said sample with a labeled, long-lasting, non-peptide receptor probe corresponding to the formula:

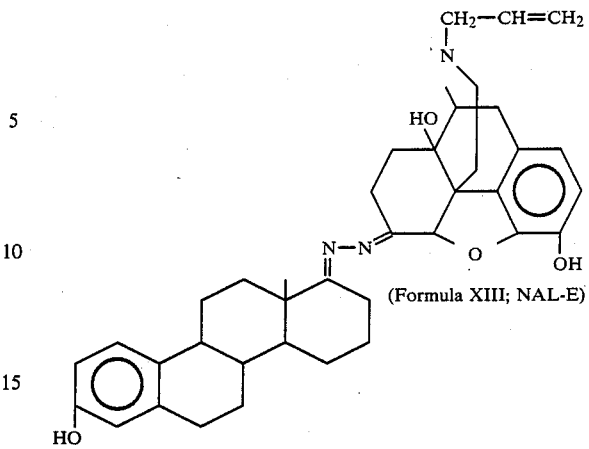
(Formula XIII; NAL-E)
and observing the emission pattern exhibited by said sample, thereby providing an indication of the location, identity or concentration of delta-type opioid receptors in the sample.
* * * * *